(12) United States Patent
Li et al.

(10) Patent No.: US 6,303,542 B1
(45) Date of Patent: Oct. 16, 2001

(54) HERBICIDAL 3-SUBSTITUTED-PHENYL-1,2,3-BENZOTRIAZIN-4-ONES

(75) Inventors: Bin Li, Liaoning (CN); Adam Chi-Tung Hsu, Lansdale, PA (US)

(73) Assignee: Rohm and Haas Company, Philadelphia, PA (US)

(*) Notice: Subject to any disclaimer, the term of this patent is extended or adjusted under 35 U.S.C. 154(b) by 0 days.

(21) Appl. No.: 09/640,644

(22) Filed: Aug. 18, 2000

(51) Int. Cl.$^7$ .................. C07D 253/08; A01N 43/707
(52) U.S. Cl. ............ 504/228; 544/52; 544/50; 544/183; 544/105; 544/92; 504/221; 504/225
(58) Field of Search ................ 544/183, 52, 92; 504/228, 221, 225

(56) References Cited

FOREIGN PATENT DOCUMENTS

| 1 271 118 | 6/1968 | (DE) . |
| 2 012 094 | 9/1971 | (DE) . |
| 241 075 A1 | 11/1986 | (DE) . |

*Primary Examiner*—John M. Ford
(74) *Attorney, Agent, or Firm*—Thomas D. Rogerson

(57) ABSTRACT

This invention relates to 3-substituted-phenyl-1,2,3-benzotriazin-4-ones which have activity as herbicides, to compositions which contain these compounds and to methods of use of these compounds.

9 Claims, No Drawings

HERBICIDAL 3-SUBSTITUTED-PHENYL-1,2,3-BENZOTRIAZIN-4-ONES

This invention relates to 3-substituted-phenyl-1,2,3-benzotriazin-4-ones which have activity as herbicides, to compositions which contain these compounds and to methods of use of these compounds.

BACKGROUND OF INVENTION

Certain 3-(2-halophenyl)-1,2,3-benzotriazin-4-ones have been disclosed as antisecretory agents (DE 2012094), or anticonvulsant agents (DE 1271118). Other benzotriazinylbenzoic acid and benzotriazinylbenzoates have been disclosed as agrochemical fungicides (DD 241075). There is no suggestion in any of these disclosures that such compounds are herbicidal.

We have discovered a class of 1,2,3-benzotriazin-4-ones which, rather than acting as fungicides, act as selective herbicides. Although a wide variety of herbicidal compounds and compositions are known for the control of unwanted vegetation, the need continues for novel and improved herbicidal compounds and compositions. This is particularly true for situations wherein a crop is infested with botanically similar weeds, for example, when a crop such as corn is infested with grassy weeds. In addition, weeds can become resistant to known herbicides over time. To overcome such resistance, economic and environmental considerations often favor herbicides having different modes of action than those currently used. There remains, therefore, a need for herbicidal agents which are as effective or more effective than presently existing compounds.

SUMMARY OF THE INVENTION

The present invention relates to herbicidal compounds and methods for their use in controlling unwanted plant species and their use in herbicidal compositions in agriculture. In particular, the present invention pertains to compounds containing a substituted phenyl ring linked to a 1,2,3-benzotriazin-4-one heterocyclic ring.

We have found that certain compounds of this invention are useful as pre-emergent and post-emergent herbicides. These compounds are represented by formula I

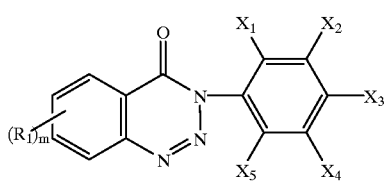

wherein m is 1 to 4;

$R_1$ is hydrogen, halo, $(C_1-C_4)$alkyl, $(C_1-C_3)$haloalkyl, $(C_1-C_3)$alkoxy, $(C_1-C_3)$haloalkoxy, nitro, cyano, phenoxy, or phenoxy substituted with halo, $(C_1-C_3)$alkyl, $(C_1-C_3)$haloalkyl, nitro, $(C_1-C_3)$alkoxy, $(C_1-C_3)$haloalkoxy, or cyano;

$X_1$ is hydrogen, halo, or acetyl;

$X_2$ is hydrogen or halo;

$X_3$ is halo, cyano, or nitro;

$X_4$ is halo, $(C_1-C_8)$alkyl, $(C_1-C_4)$haloalkyl, $(C_1-C_4)$alkoxy, $(C_3-C_6)$cycloalkoxy, $(C_2-C_6)$alkenyloxy, $(C_3-C_6)$alkynyloxy, $(C_1-C_4)$alkoxycarbonyl, $(C_2-C_6)$alkenyloxycarbonyl, $(C_3-C_6)$alkynyloxycarbonyl, $(C_1-C_8)$alkylsulfonylamino, $(C_1-C_8)$alkylsulfonylalkylamino, $(C_1-C_4)$alkoxycarbonylmethoxy, or $(C_1-C_4)$alkoxycarbonylethoxy;

$X_5$ is hydrogen or halo;

provided that:

a) when $X_1$ is halo or acetyl and $X_2$ and $X_5$ are hydrogen, then $X_3$ and $X_4$ form a 5- or 6-membered heterocyclic ring fused to the phenyl ring structure to form a bicyclic moiety having the structure

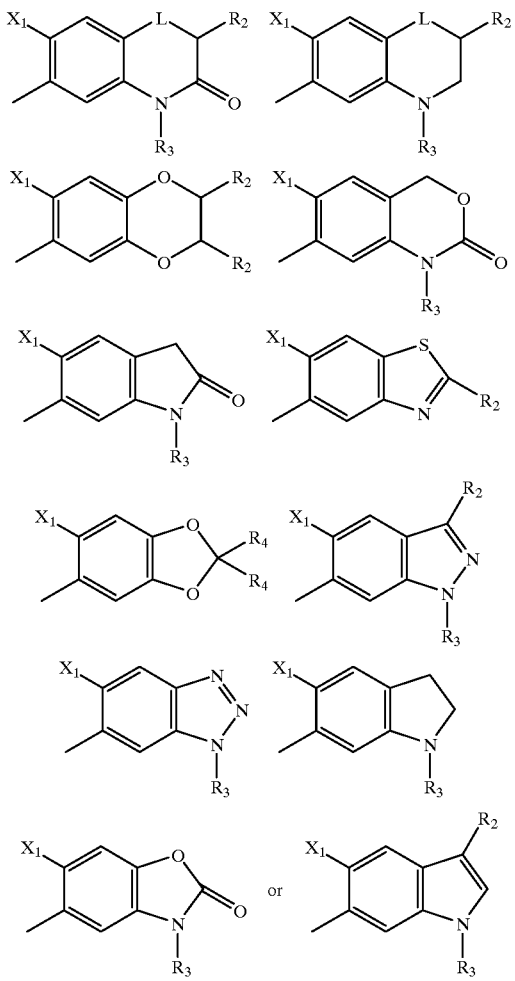

wherein

L is oxygen (O) or sulfur (S);

$R_2$ is hydrogen or alkyl;

$R_3$ is hydrogen; $(C_1-C_6)$alkyl, $(C_1-C_6)$haloalkyl, $(C_3-C_6)$alkenyl, $(C_3-C_6)$alkynyl; $(C_1-C_6)$alkoxyalkyl; $(C_3-C_6)$alkenyloxyalkyl; $(C_3-C_6)$alkynyloxyalkyl; cyanoalkyl; amino, or hydroxy;

$R_4$ is hydrogen, $(C_1-C_3)$alkyl, or fluorine; or b) when $X_1$ and $X_3$ are halo and $X_2$ is hydrogen, then $X_4$ and $X_5$ form a 5- or 6-membered heterocyclic ring fused to the phenyl ring structure to form a bicyclic moiety having the structure

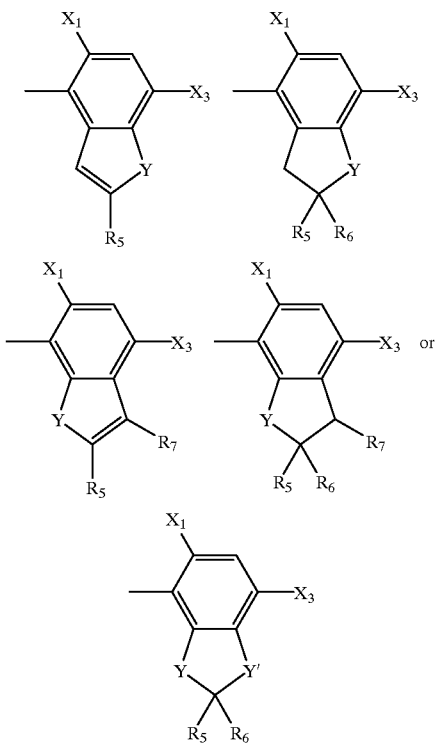

wherein
- Y is oxygen, sulfur or a group of —NR$_6$ in which R$_6$ is hydrogen, (C$_1$–C$_6$)alkyl, (C$_3$–C$_5$)alkenyl or (C$_3$–C$_6$)alkynyl;
- Y' is oxygen, sulfur, a group of —NR$_6$, or a group of —CO;
- R$_5$ is hydrogen, halo, (C$_1$–C$_6$)alkyl, (C$_3$–C$_6$)cycloalkyl, (C$_2$–C$_6$)alkenyl, or (C$_3$–C$_6$)alkynyl, (C$_1$–C$_6$)haloalkyl, (C$_1$–C$_6$)alkoxy, cyano, (C$_1$–C$_6$) hydroxyalkyl, a group of —CO$_2$R$_8$, a formyl group, an acyl group, (C$_1$–C$_6$) alkylthio, (C$_1$–C$_6$)alkylsulfinyl, (C$_1$–C$_6$)alkylsulfonyl, (C$_1$–C$_6$)haloalkylthio, (C$_1$–C$_6$)haloalkylsulfinyl, (C$_1$–C$_6$)haloalkylsulfonyl, or a carboxyl group;
- R$_6$ is hydrogen, (C$_1$–C$_6$)alkyl, (C$_3$–C$_6$)alkenyl, or (C$_3$–C$_6$)alkynyl;
- R$_7$ is hydrogen, halo, (C$_1$–C$_6$)alkyl, (C$_1$–C$_6$)haloalkyl, an acyl group, or a nitro;

and agronomically acceptable salts thereof.

The term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl and the like.

The term "cycloalkyl" refers to a cyclic aliphatic ring structure such as cyclopropane, cyclobutane, cyclopentane, cyclohexane, cycloheptane, cyclooctane and the like.

The term "haloalkyl" refers to an alkyl group substituted with one or more halo groups.

The term "halo" refers to fluoro, chloro, bromo or iodo.

The term "alkylsulfonylalkyl" refers to an alkyl group substituted with an alkylsulfonyl (alkyl-SO$_2$) group, for example methylsulfonylmethyl.

The term "alkylsulfinylalkyl" refers to an alkyl group substituted with an alkylsulfinyl (alkyl-SO) group, for example methylsulfinylmethyl.

The term "alkenyl" refers to an ethylenically unsaturated hydrocarbon group, straight or branched, having 1 or 2 ethylenic bonds.

The term "haloalkenyl" refers to an alkenyl group substituted with one or more halo groups.

The term "alkynyl" refers to an unsaturated hydrocarbon group, straight or branched, having 1 or 2 acetylenic bonds.

The term "alkoxy" includes both branched and straight chain alkyl groups attached to a terminal oxygen atom. Typical alkoxy groups include methoxy, ethoxy, n-propoxy, isopropoxy, tert-butoxy and the like.

The term "haloalkoxy" refers to an alkoxy group substituted with one or more halo groups.

The term "alkylthio" includes both branched and straight chain alkyl groups attached to a terminal sulfur atom.

The term "haloalkylthio" refers to an alkylthio group substituted with one or more halo groups.

Acceptable acids that may form agronomically acceptable salts of the compounds of the present invention include, for example, hydrochloric acid, hydrobromic acid, hydroiodic acid, sulfuric acid, nitric acid, phosphoric acid, oxalic acid, acetic acid, propionic acid, glycolic acid, methanesulfonic acid, toluenesulfonic acid, benzenesulfonic acid, (C$_2$–C$_{20}$) alkylbenzenesulfonic acid, sodium hydrogen sulfate and methyl hydrogen sulfate.

Other agronomically acceptable salts may be formed by complexation of the compounds of the current invention with metal salts such as zinc chloride or iron chloride.

Preferred compounds include compounds of the formula

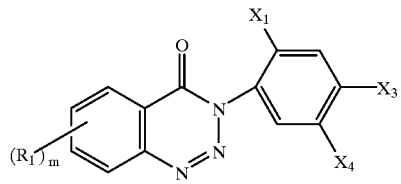

wherein
- m is 1 to 4;
- R$_1$ is hydrogen, halo, (C$_1$–C$_4$)alkyl, (C$_1$–C$_3$)haloalkyl, (C$_1$–C$_3$)alkoxy, (C$_1$–C$_3$)haloalkoxy, nitro, cyano, phenoxy, or phenoxy substituted with halo, (C$_1$–C$_3$) alkyl, (C$_1$–C$_3$)haloalkyl, nitro, (C$_1$–C$_3$)alkoxy, (C$_1$–C$_3$) haloalkoxy, or cyano;
- X$_1$ is hydrogen, halo, or acetyl;
- X$_2$ is hydrogen or halo;
- X$_3$ is halo, cyano, or nitro;
- X$_4$ is halo, (C$_1$–C$_8$)alkyl, (C$_1$–C$_4$)haloalkyl, (C$_1$–C$_4$) alkoxy, (C$_3$–C$_6$)cycloalkoxy, (C$_2$–C$_6$)alkenyloxy, (C$_3$–C$_6$)alkynyloxy, (C$_1$–C$_4$)alkoxycarbonyl, (C$_2$–C$_6$) alkenyloxycarbonyl, (C$_3$–C$_6$)alkynyloxycarbonyl, (C$_1$–C$_8$)alkylsulfonylamino, (C$_1$–C$_8$) alkylsulfonylalkylamino, (C$_1$–C$_4$) alkoxycarbonylmethoxy, or (C$_1$–C$_4$) alkoxycarbonylethoxy;
- X$_5$ is hydrogen or halo;

and agronomically acceptable salts thereof.

Even more preferred compounds include compounds of the formula

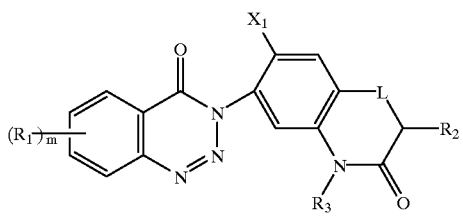

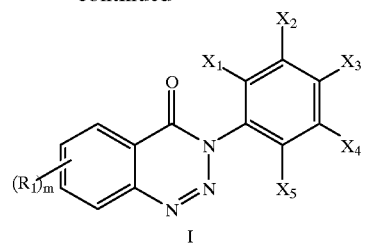

wherein m=1 to 4;

$R_1$ is hydrogen, halo, $(C_1-C_4)$alkyl, $(C_1-C_3)$haloalkyl, $(C_1-C_3)$alkoxy, $(C_1-C_3)$haloalkoxy, nitro, cyano, phenoxy, or phenoxy substituted with halo, $(C_1-C_3)$alkyl, $(C_1-C_3)$haloalkyl, nitro, $(C_1-C_3)$alkoxy, $(C_1-C_3)$haloalkoxy, or cyano;

L is O or S;

$X_1$ is H, Cl or F $R_2$ is H or $(C_1-C_3)$alkyl; and $R_3$ is $(C_1-C_6)$alkyl, $(C_1-C_6)$haloalkyl, $(C_3-C_6)$alkenyl, halo$(C_3-C_6)$alkenyl, $(C_3-C_6)$alkynyl; halo$(C_3-C_6)$alkynyl; alkoxyalkyl; alkenyloxyalkyl; alkynyloxyalkyl; cyanoalkyl; amino, or hydroxy; and agronomically acceptable salts thereof.

General Synthetic Methods

The compounds of formula I of the present invention can be prepared by the following processes:

Scheme 1:

Benzoic acids (when X is hydroxy) or their acyl chlorides (when X is chloride) II are reacted with anilines III in a solvent such as chloroform, dichloromethane, carbon tetrachloride, hexane, benzene, toluene, tetrahydrofuran, dioxane, acetone or methyl ethyl ketone to yield compounds IV, optionally in the presence of the bases such as $Et_3N$, pyridine, NaOH, KOH, $Na_2CO_3$, $K_2CO_3$, $NaHCO_3$ at a temperature from $-40°$ C. to the boiling point of the solvent for 3 minutes to 48 hours.

Anilines may be obtained from the nitro substituted benzene (made by known methods such as those described in EP 0 083 055 A2) by reacting with hydrogen or reductive metals such as, for example, iron, zinc, and titanium, etc. in compatible solvents, such as chloroform, dichloromethane, carbon tetrachloride, hexane, benzene, toluene, tetrahydrofuran, dioxane, acetone, methyl ethyl ketone, ethanol or combined with an inorganic acid such as hydrochloric acid, at a temperature from $-40°$ C. to the boiling point of the solvent for 3 minutes to 48 hours.

Intermediate V from IV may employ similar procedures to prepare anilines III.

Intermediate V also may be obtained from the following reactions:

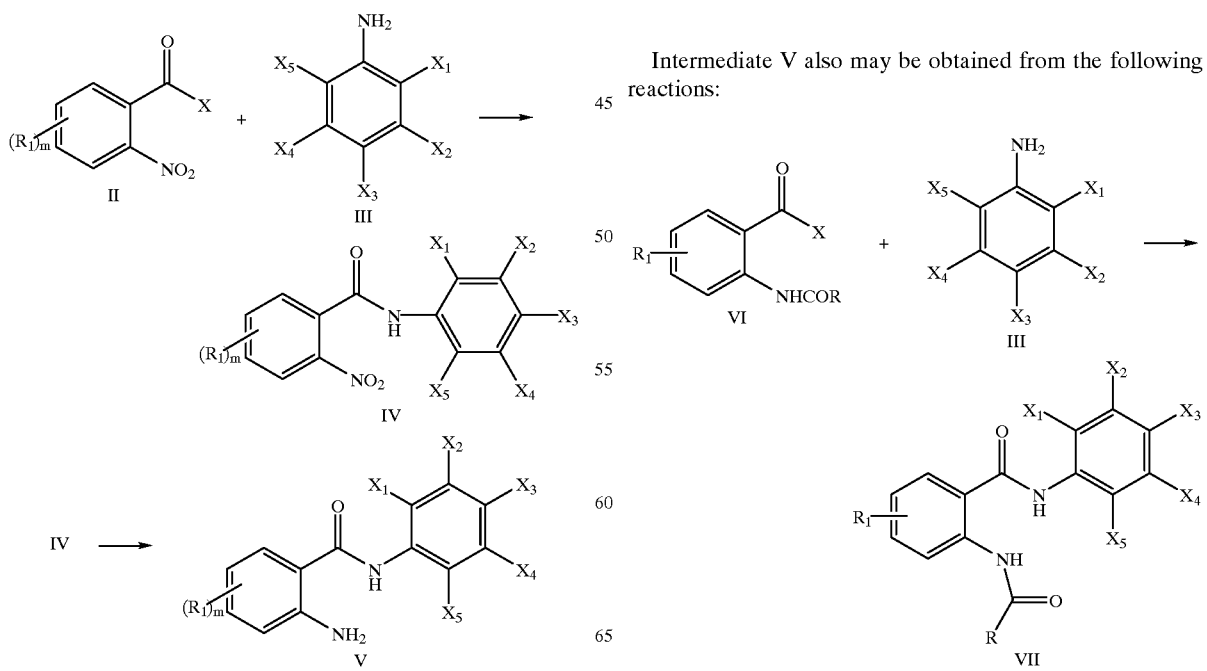

VII →
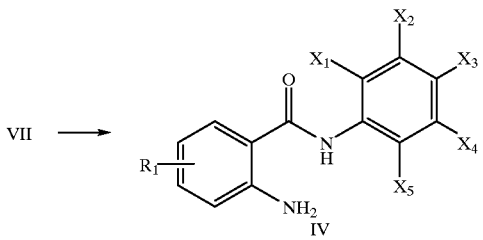

Intermediates VII may be obtained from reacting VI with anilines III in a solvent such as chloroform, dichloromethane, carbon tetrachloride, hexane, benzene, toluene, tetrahydrofuran, dioxane, acetone or methyl ethyl ketone to yield compounds VII, optionally in the presence of the bases such as $Et_3N$, pyridine, NaOH, KOH, $Na_2CO_3$, $K_2CO_3$, $NaHCO_3$ at a temperature from −40° C. to the boiling point of the solvent for 3 minutes to 48 hours.

Intermediates VII are reacted with an inorganic acid such as hydrochloric acid without or in an organic solvent such as chloroform, dichloromethane, carbon tetrachloride, hexane, benzene, toluene, tetrahydrofuran, dioxane, acetone or methyl ethyl ketone to yield intermediates IV at a temperature from ambient temperature to the boiling point of the solvent for 3 minutes to 48 hours.

Intermediates IV are reacted with nitrous acid in a solvent such as water, chloroform, dichloromethane, carbon tetrachloride, hexane, benzene, toluene, tetrahydrofuran, dioxane, acetone or methyl ethyl ketone to yield compounds I at a temperature from −40° C. to the boiling point of the solvent for 3 minutes to 48 hours.

Scheme 2:

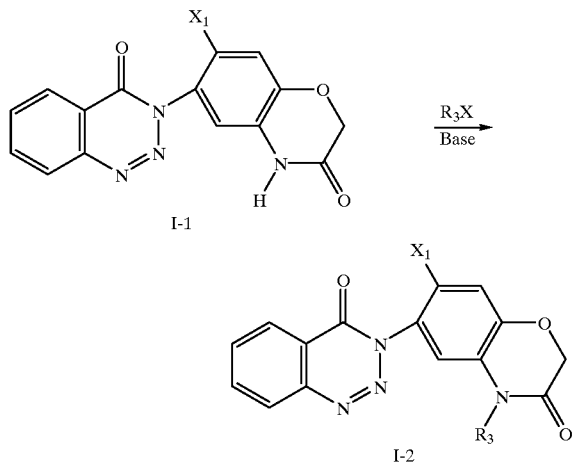

Certain compounds of the Formula I may be obtained by reacting compounds of the Formula I-1, which can be prepared according to Scheme 1 with alkyl halides or alkyl sulfonylesters in a solvent inert under the reaction conditions, e.g., chloroform, dichloromethane, carbon tetrachloride, hexane, benzene, toluene, ethyl acetate, acetone, dimethylformamide, tetrahydrofuran or dioxane, optionally in the presence of a base such as triethylamine, pyridine, sodium hydroxide, potassium hydroxide, sodium carbonate, potassium carbonate, sodium bicarbonate or sodium hydride at a temperature from −40° C. to the boiling point of the solvent for 3 minutes to 48 hours. Alkyl halides or alkyl sulfonylesters are commercially available or can be prepared by known methods.

Examples of compounds of the Formula I, prepared according to the above general methods, are listed in Table 1a, Table Ib and Table 2. The preparation of several specific examples in this invention is described below in more detail.

1. Preparation of Compound No 49

A solution of 2-nitro-benzoyl chloride (2.04 g, 90% purity, 10 mmol) in $CH_2Cl_2$ (20 mL) was added dropwise into a mixture of 7-fluoro-6-amino-2H-1,4-benzoxazin-3-(4H)-one (1.78 g, 10 mmol) and triethylamine (1.1 g, 11 mmol) in $CH_2Cl_2$ (20 mL) over 10 min with ice-water bath cooling. The reaction mixture was then stirred at room temperature overnight. The mixture was poured into water and the resulting precipitate was collected by suction-filtration and washed with hexane and then water to give 7-fluoro-6-(2-nitrobenzoyl)amino-2H-1,4-benzoxazin-3-(4H)-one, 2.9 g (yield: 92%) as a solid: mp >248° C.

A solution of 2 N $NH_4Cl$ (15 mL, 27 mmol) was added into a solution of the above intermediate (1.1 g, 3.4 mmol) in THF (25 mL) in an ice-water bath. Zinc dust (1.5 g, 16 mmol) was added portionwise over 15 min. The reaction mixture was stirred at room temperature for 3 h and then the insoluble materials were removed by suction-filtration and washed with EtOAc and water. The filtrate was extracted with EtOAc and the combined organic layer was washed sequentially with water and brine. The organic extracts were dried over $Na_2SO_4$ and filtered. After removing the solvents by evaporation, 7-fluoro-6-(2-aminobenzoyl)amino-2H-1,4-benzoxazin-3-(4H)-one (0.7 g, 70%) was obtained as a solid: mp 251–252° C.

A solution of 3 N $NaNO_2$ (0.6 mL, 2.6 mmol) was added into a slurry of 7-fluoro-6-(2-aminobenzoyl)amino-2H-1,4-benzoxazin-3-(4H)-one (0.6 g, 2 mmol) in 2 N HCl (7 mL) with stirring in an ice-water bath. The reaction mixture was stirred at room temperature for 3 h and the resulting precipitate was collected by suction-filtration and washed with water. The compound, 3-[7-fluoro-2H-1,4benzoxazin-3(4H-one-6]-1,2,3-benzotriazin-4-one (0.55 g, 90%) was obtained as a solid: mp >252° C.

2. Preparation of Compound 62

Sodium hydride (0.070 g 60% in oil, 1.8 mmol) was added into a mixture of compound 49 (0.45 g, 1.5 mmol) in DMF (15 mL) with stirring in an ice-water bath. The reaction mixture was stirred at room temperature for 10 min and then propargyl bromide in toluene (0.25 g, 80%, 1.6 mmol) was added. The reaction mixture was stirred at room temperature overnight and then combined with EtOAc (100 mL), washed sequentially with water and brine, and dried over $Na_2SO_4$. The titled compound, 3-[7-fluoro-4-(2-propynyl)-2H-1,4-benzoxazin-3(4H-one-6]-1,2,3-benzotriazin-4-one, 0.3 g yield: 60%) was obtained as a solid after solvents were removed in vacuum, mp 246–248° C.

TABLE 1a

![structure]

| No | R₁ | X₁ | X₂ | X₃ | X₄ | X₅ | mp (°C.) |
|---|---|---|---|---|---|---|---|
| 1 | H | H | H | H | H | H | 149–150 |
| 2 | H | F | H | H | H | H | 140–141 |
| 3 | H | Cl | H | H | H | H | 116–117 |
| 4 | H | Br | H | H | H | H | 105–106 |
| 5 | H | I | H | H | H | H | 148–149 |
| 6 | H | CH₃ | H | H | H | H | 163–164 |
| 7 | H | CF₃ | H | H | H | H | 143–144 |
| 8 | H | CN | H | H | H | H | 158–159 |
| 9 | H | CH₃O | H | H | H | H | 150–151 |
| 10 | H | H | F | H | H | H | 133–134 |
| 11 | H | H | Cl | H | H | H | 140–141 |
| 12 | H | H | Br | H | H | H | 156–157 |
| 13 | H | H | I | H | H | H | 143–144 |
| 14 | H | H | CH₃ | H | H | H | 148–149 |
| 15 | H | H | CF₃ | H | H | H | 134–135 |
| 16 | H | H | CN | H | H | H | 192–193 |
| 17 | H | H | CH₃O | H | H | H | 123–124 |
| 18 | H | H | H | F | H | H | 147–148 |
| 19 | H | H | H | Cl | H | H | 183–184 |
| 20 | H | H | H | Br | H | H | 194–195 |
| 21 | H | H | H | I | H | H | 134–135 |
| 22 | H | H | H | CH₃ | H | H | 138–139 |
| 23 | H | H | H | CF₃ | H | H | 231–232 |
| 24 | H | H | H | CN | H | H | 226–227 |
| 25 | H | H | H | CH₃O | H | H | 155–156 |
| 26 | H | F | H | Cl | H | H | 144–145 |
| 27 | H | Cl | H | Cl | H | H | 125–126 |
| 28 | H | Cl | H | F | H | H | 174–175 |
| 29 | H | CH₃ | H | H | CH₃ | H | |
| 30 | H | CH₃ | H | CH₃ | H | H | 126–127 |
| 31 | H | H | Cl | Cl | H | H | 210–211 |
| 32 | H | H | Cl | H | Cl | H | 219–220 |
| 33 | H | F | H | F | F | H | 168–169 |
| 34 | H | F | H | CN | F | H | 203–205 |
| 35 | H | Cl | H | F | CH₃ | H | 157–158 |
| 36 | H | F | H | Cl | cyclopentyloxy | H | 133–134 |
| 37 | H | F | H | Cl | propargyloxy | H | 185–186 |
| 38 | H | F | H | Cl | C₂H₅OCO₂— | H | 128–129 |
| 39 | H | F | H | Cl | (CH₃)₂CH₂OCO— | H | 183–184 |
| 40 | H | F | H | Cl | C₂H₅OCOCH₂O— | H | 118–120 |
| 41 | H | Cl | H | Cl | propargyloxy | H | 151–152 |
| 42 | 8(7?)-Cl | F | H | Cl | propargyloxy | H | 158–160 |
| 43 | 5-CH₃ | F | H | Cl | propargyloxy | H | oil |
| 44 | 7-CF₃ | F | H | Cl | propargyloxy | H | 124–125 |
| 45 | 6-A* | F | H | Cl | H | H | 153–154 |
| 46 | H | F | H | F | H | F | 173–174 |
| 47 | H | Cl | H | Cl | H | Cl | 126–127 |
| 48 | H | Br | H | Br | H | Br | 128–129 |

*A =

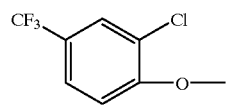

TABLE 1b

| Compound No | Structure | mp(°C.) |
|---|---|---|
| 49 | (structure) | >252 |
| 78 | (structure) | 208–209 |
| 79 | (structure) | 203–204 |

TABLE 2

| No | $R_1$ | $R_2$ | mp (°C.) |
|---|---|---|---|
| 49 | H | H | >252 |
| 50 | H | $CH_3$ | 255–257 |
| 51 | H | $C_2H_5$ | 222–224 |
| 52 | H | $NCCH_2$ | 240–242 |
| 53 | H | $FCH_2CH_2$ | 215–217 |
| 54 | H | $CF_3CH_2$ | 243–245 |
| 55 | H | $ClCH_2CH_2$ | 190–192 |
| 56 | H | $BrCH_2CH_2$ | 219–220 |
| 57 | H | $CH_3OCH_2$ | 213–215 |
| 58 | H | $CH_3SCH_2$ | 204–207 |
| 59 | H | $CH_3CH_2CH_2$ | 174–176 |
| 60 | H | allyl | 212–214 |
| 61 | H | 2-chloroallyl | 195–197 |
| 62 | H | propargyl | 246–248 |
| 63 | H | $CH_3CH(CN)$ | 165–170 |
| 64 | H | $FCH_2CH_2CH_2$ | 184–186 |
| 65 | H | $ClCH_2CH_2CH_2$ | 129–131 |
| 66 | H | $CHF_2CF_2CH_2$ | 195–197 |
| 67 | H | $CH_3OCH_2CH_2$ | 196–199 |
| 68 | H | $CH_3CH_2OCH_2$ | 178–180 |
| 69 | H | $CH_3CH_2CH_2CH_2$ | 160–162 |
| 70 | H | $(CH_3)_2CHCH_2$ | 180–182 |
| 71 | H | 2-$CH_3$-allyl | 200–202 |
| 72 | H | 1-$CH_3$-propargyl | 95–97 |
| 73 | H | 2-butynyl | 248–250 |
| 74 | H | $C_2H_5OCOCH_2$ | 174–176 |
| 75 | H | $CH_3CH_2CH_2CH_2CH_2$ | 131–133 |
| 76 | H | 2-pentynyl | 190–192 |
| 77 | 7-$CF_3$ | H | 157–158 |

Herbicidal Activity

When a compound of formula I of the present invention is used as an herbicide, the active ingredient can be used in a suitable formulation depending upon the particular purpose and by a suitable application method. Usually, the active ingredient is diluted with an inert liquid or solid carrier, and used in the form of a formulation such as a dust, a wettable powder, an emulsifiable concentrate, aqueous or oil suspension, pellets, granules, etc., If desirable one may also add one or more surfactants and/or other additives. Furthermore, one of ordinary skill in the art will recognize that a compound of the present invention may be used in combination with an insecticide, a nematocide, a fungicide, other herbicides, a plant growth controlling agent, a fertilizer, etc.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier materials or liquid carrier materials, of the type usable in conventional pesticide compositions or formulations. By "agronomically acceptable carrier" is meant any substance which can be used to dissolve, disperse of diffuse the active ingredient in the composition without impairing the active ingredient's effectiveness and which by itself has no significant detrimental effect on the soil, equipment, desirable plants, or agronomic environment. If desired, adjuvants such as surfactants, stabilizers, antifoam agents and anti-drift agents may also be combined. Such adjuvants commonly used in the art can be found in *McCutcheon's Emulsifiers and Detergents, McCutcheon's Emulsifiers and Detergents/Functional Materials*, and *McCutcheon's Functional Materials* all published annually by McCutcheon Division of MC Publishing Company (New Jersey) and Farm Chemicals Handbook published by Meister Publishing Company (Ohio). Compositions and formulations according to the present invention may also include other known pesticidal compounds. This expands the spectrum of activity of the preparation and may give rise to synergism.

The formulations may contain from about 0.1% to 99% by weight of active ingredient(s) and at least one of (a) 0.1% to 20% surfactant(s) and/or (b) 1% to 99.9% solid or liquid diluent(s).

If the compound of formula(I) is formulated with an additional herbicide, the concentration of active ingredient(s) in the compositions can vary within a wide range, depending on the active compound, the applications for which they are destined, the environmental conditions, and the kind of formulation. The concentration of active ingredient(s) in the compositions is generally between 1% to 95%, preferably between 5% to 60%. In use, unwanted vegetation is controlled by applying to the vegetation, or to the soil wherein the unwanted vegetation grows, an herbicidally effective amount of a compound of formula I or a composition comprising one or more compounds of formula I and an agronomically acceptable carrier. The compounds and compositions of this invention can be diluted or applied as is to plant foliage and/or soil as aqueous sprays by methods commonly employed, such as conventional high-volume hydraulic sprays, low-volume sprays, air-blast, and aerial sprays. The dilution and rate of application will depend upon the type of equipment employed, the method and frequency of application desired, the herbicide application rate, and the weeds to be controlled. The compositions can be mixed with fertilizers or fertilizing materials before their application.

The effective dose of the compounds of the present invention is usually within a range of from 1 g/ha to 3 kg/ha, preferably from 5 g/ha to 500 g/ha.

The following examples illustrate several aspects of this invention in detail:

Biological Testing

Listed below, a typical planting design for the test, consisting of four monocot weeds, four dicot weeds and one sedge weed.

| Common Name | Scientific Name |
|---|---|
| Grasses | |
| Barnyardgrass | *Echiniochloa crusgalli* |
| Crabgrass (large) | *Digitaria sanguinalis* |
| Foxtail, (green) | *Setaria viridis* |
| Perennial Ryegrass | *Lolium perenne* |
| Sedges | |
| Nutsedge, (yellow) | *Cyperus esculentus* |
| Broad Leaf Weeds | |
| Hairy Beggarticks | *Bidens pilosa* |
| Nightshade, (black) | *Solanum nigrum* |
| Smartweed, (pale) | *Polygonum lapathifolium* |
| Velvetleaf | *Abutilon theophrasti* |

For each compound, evaluation tests were carried out according to the following procedures:

For preemergence tests, immediately after planting, the test compound was sprayed directly onto the soil surface in flats or pots. The flats or pots were placed in a greenhouse and then watered. For postemergence tests, seeds were allowed to germinate and grow for 10 to 21 days before application. The test plants were selected for uniformity, slize, and stage of development. The test plants were then treated with the test compound, returned to a greenhouse and watered. Untreated plants were used as a comparison.

The compound to be evaluated was dissolved in an appropriate solvent, usually acetone, or a formulation of the evaluated compound as described above, was added to water, and sprayed over the flats or pots using a carrier volume equivalent to 187 or 468 liters per hectare to give a rate of application in grams per hectare (g/ha). About two or four weeks after application of the test compound, the state of the plant was observed. Each species was evaluated on a scale of 0–100 in which 0 equals no activity and 100 equals total control. Some of the test results are shown in Table 3

TABLE 3

Herbicidal Activity Test Results of 3-Phenyl-1,2,3-Benzotriazin-4-ones (pre/post) (1200 g/ha)

| No | BYG | FOX | MA | TOM | VEL |
|---|---|---|---|---|---|
| 1 | 0/0 | 0/0 | 0/0 | 0/0 | 0/40 |
| 2 | 0/15 | 0/0 | 0/0 | 0/15 | 0/60 |
| 5 | 0/0 | 0/60 | 0/0 | 0/0 | 0/30 |
| 9 | 0/0 | 0/20 | 0/0 | 0/0 | 0/0 |
| 14 | 0/0 | 60/0 | 0/0 | 0/0 | 0/0 |
| 15 | 0/0 | 75/0 | 0/0 | 0/0 | 0/0 |
| 18 | 0/0 | 0/0 | 0/0 | 0/15 | 0/98 |
| 19 | 0/10 | 0/0 | 0/0 | 0/50 | 0/90 |
| 22 | 0/0 | 0/0 | 0/0 | 0/0 | 0/80 |
| 24 | 0/0 | 0/0 | 0/0 | 0/0 | 0/70 |
| 26 | 10/98 | 98/90 | 0/0 | 60/95 | 15/100 |
| 27 | 20/0 | 20/0 | 0/0 | 10/10 | 10/80 |
| 28 | 0/0 | 0/0 | 0/0 | 0/0 | 0/80 |
| 31 | 0/0 | 0/0 | 0/0 | 10/0 | 10/0 |
| 33 | 0/20 | 0/0 | 0/0 | 0140 | 0/100 |
| 34 | 0/0 | 0/0 | 0/0 | 0/80 | 0/80 |
| 35 | 0/0 | 0/0 | 0/0 | 0/0 | 0/40 |
| 36 | 0/70 | 90/50 | 0/0 | 0/25 | 80/100 |
| 37 | 20/99 | 100/98 | 0/100 | 100/100 | 85/100 |
| 38 | 0/0 | 0/0 | 0/0 | 0/20 | 0/80 |
| 39 | 0/75 | 0/90 | 0/0 | 0/100 | 0/100 |
| 40 | 0/60 | 0140 | 0/80 | 0/85 | 0/100 |
| 42 | 0/60 | 0/30 | 0/0 | 0/100 | 0/100 |
| 43 | 0/80 | 0/85 | 0/0 | 0/20 | 0/100 |
| 44 | 0/80 | 0/95 | 0/95 | 0/80 | 0/100 |
| 46 | 0/0 | 0/0 | 0/0 | 0/85 | 0/90 |
| 49 | 0/0 | 0/0 | 0/0 | 0/0 | 0/20 |
| 50 | 0/0 | 0/30 | 0/0 | 0/85 | 0/70 |
| 51 | 95/95 | 80/95 | 0/80 | 85/90 | 80/100 |
| 52 | 80/80 | 80/80 | 20/95 | 90/95 | 60/95 |
| 53 | 60/85 | 100/100 | 0/100 | 100/100 | 100/100 |
| 54 | 80/70 | 90/95 | 0/80 | 100/100 | 100/100 |
| 55 | 30/90 | 80/90 | 20/100 | 70/100 | 100/100 |
| 56* | 0/60 | 20/6 | — | — | 40/100 |
| 57 | 85/60 | 30/0 | 0/0 | 100/90 | 100/100 |
| 58 | 20/80 | 80/95 | 0/85 | 90/90 | 20/100 |
| 59* | 60/80 | 100/80 | — | — | 100/100 |
| 60 | 85/90 | 90/95 | 0/80 | 100/100 | 100/100 |
| 61 | 30/90 | 85/20 | 0/60 | 20/80 | 100/100 |
| 62 | 95/85 | 90/95 | 60/100 | 90/90 | 90/100 |
| 63 | 0/70 | 95/60 | 0/80 | 80/80 | 0/100 |
| 64 | 20/90 | 70/90 | 0/90 | 90/95 | 0/95 |
| 65 | 20/95 | 60/30 | 0/0 | 60/80 | 40/100 |
| 66 | 30/90 | 90/95 | 0/30 | 90/90 | 0/100 |
| 67 | 95/95 | 85/90 | 20/70 | 70/100 | 100/100 |
| 68 | 95/95 | 20/30 | 0/0 | 20/95 | 70/100 |
| 69 | 30/95 | 0/90 | 0/30 | 0/60 | 40/100 |
| 70 | 30/85 | 80/90 | 0/15 | 99/95 | 20/95 |
| 71 | 20/85 | 90/80 | 0/90 | 100/95 | 0/100 |
| 72 | 95/80 | 95/95 | 20/100 | 100/100 | 100/100 |
| 73 | 20/80 | 90/30 | 0/0 | 0/40 | 0/95 |
| 74 | 0/0 | 0/0 | 0/0 | 0/0 | 0/40 |
| 75 | 0/60 | 0/0 | 0/0 | 0/70 | 0/70 |
| 76 | 0/0 | 0/0 | 0/0 | 0/0 | 0/60 |
| 78 | 0/0 | 0/30 | 0/0 | 0/20 | 0/80 |

*600 g/ha

We claim:
1. A compound of the formula:

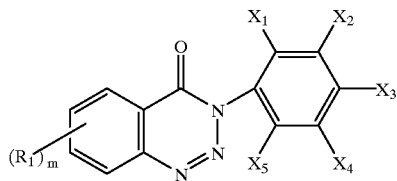

wherein m is from 1 to 4;

$R_1$ is hydrogen, halo, $(C_1-C_4)$alkyl, $(C_1-C_3)$haloakyl, $(C_1-C_3)$alkoxy, $(C_1-C_3)$haloalkoxy, nitro, cyano, phenoxy, or phenoxy substituted with halo, $(C_1-C_3)$alkyl, $(C_1-C_3)$haloalkyl, nitro, $(C_1-C_3)$alkoxy, $(C_1-C_3)$haloalkoxy, or cyano;

$X_1$ is hydrogen, halo, or acetyl;

$X_2$ is hydrogen or halo;

$X_3$ is halo, cyano, or nitro;

$X_4$ is halo, $(C_1-C_8)$alkyl, $(C_1-C_4)$haloalkyl, $(C_1-C_4)$alkoxy, $(C_3-C_6)$cycloalkoxy, $(C_2-C_6)$alkenyloxy, $(C_3-C_6)$akynyloxy, $(C_1-C_4)$alkoxycarbonyl, $(C_2-C_6)$alkenyloxycarbonyl, $(C_3-C_6)$alkynyloxycarbonyl, $(C_1-C_8)$alkylsulfonylamino, $(C_1-C_8)$alkylsulfonylalkyamino, $(C_1-C_4)$alkoxycarbonylmethoxy, or $(C_1-C_4)$alkoxycarbonylethoxy; and $X_5$ is hydrogen or halo;

or wherein:

a) $X_1$ is halo or acetyl, $X_2$ and $X_5$ are hydrogen, and $X_3$ and $X_4$ form a 5- or 6-membered heterocyclic ring fused to the phenyl ring structure to form a bicyclic moiety having the structure

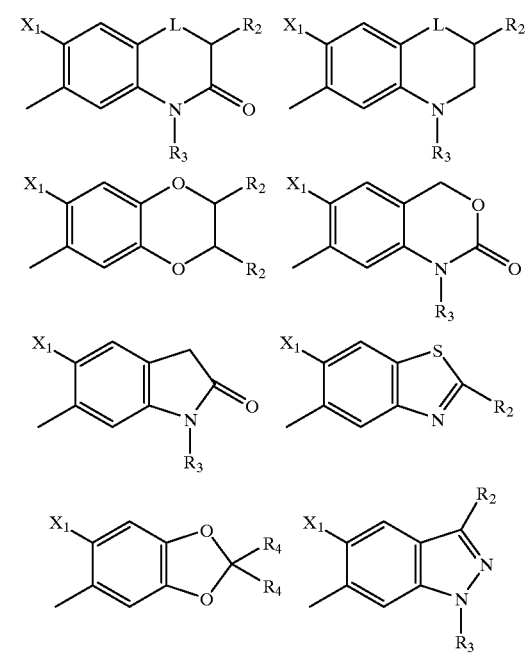

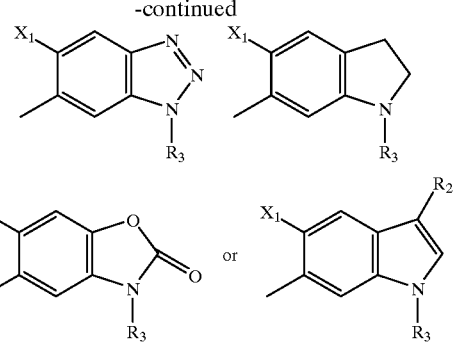

wherein

L is oxygon (O) or sulfur (S);

$R_2$ is hydrogen or alkyl;

$R_3$ is hydrogen, $(C_1-C_6)$alkyl, $(C_1-C_6)$haloalkyl, $(C_3-C_6)$alkenyl, $(C_3-C_6)$alkynyl, $(C_1-C_6)$alkoxyalkyl, $(C_3-C_6)$alkenyloxyalkyl, $(C_3-C_6)$alkynyloxyalkyl, cyanoalkyl, amino, or hydroxy;

$R_4$ is hydrogen, $(C_1-C_3)$alkyl, or fluorine; or b) $X_1$ and $X_3$ are halo, $X_2$ is hydrogen, and $X_4$ and $X_5$ form a 5- or 6-membered heterocyclic ring fused to the phenyl ring structure to form a bicyclic moiety having the structure

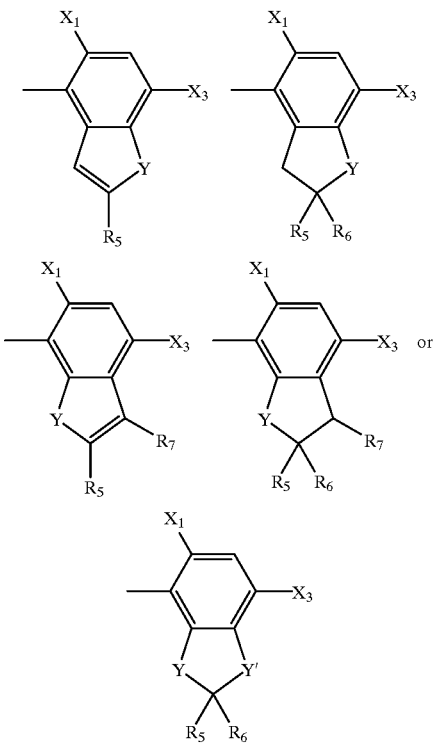

wherein

Y is oxygen, sulfor or a group of $-NR_6$ in which $R_6$ is hydrogen, $(C_1-C_6)$alkyl, $(C_3-C_5)$alkenyl or $(C_3-C_6)$alkynyl;

Y' is oxygen, sulfor, a group of $-NR_6$, or a group of $-CO$;

$R_5$ is hydrogen, halo, $(C_1-C_6)$alkyl, $(C_3-C_6)$cycloalkyl, $(C_2-C_6)$alkenyl, or $(C_3-C_6)$alkynyl, $(C_1-C_6)$haloalkyl, $(C_1-C_6)$alkoxy, cyano, $(C_1-C_6)$hydroxyalkyl, a group of —$CO_2R_8$, a formyl group, an acyl group, ($C_1$–$C_6$) alkylthio, ($C_1$–$C_6$)alkylsulfinyl, ($C_1$–$C_6$)alkylsulfonyl, ($C_1$–$C_6$)haloalkylthio, ($C_1$–$C_6$)haloalkylsulfinyl, ($C_1$–$C_6$)haloalkylsulfonyl, or a carboxyl group;

$R_6$ is hydrogen, ($C_1$–$C_6$)alkyl, ($C_3$–$C_6$)alkenyl, or ($C_3$–$C_6$)alkynyl;

$R_7$ is hydrogen, halo, ($C_1$–$C_6$)alkyl, ($C_1$–$C_6$)haloalkyl, an acyl group, or nitro;

provided that when $X_1$ is halo and $X_2$ and $X_3$ are hydrogen or halo, then $X_4$ and $X_5$ are other than hydrogen, halo, ($C_1$–$C_8$)alkyl, or ($C_1$–$C_4$)haloalkyl;

and the agronomically acceptable salts thereof.

2. The compound of claim 1, wherein:

m is from 1 to 4;

$R_1$ is hydrogen, halo, ($C_1$–$C_4$)alkyl, ($C_1$–$C_3$)haloalkyl, ($C_1$–$C_3$)alkoxy, ($C_1$–$C_3$)haloalkoxy, nitro, cyano, phenoxy, or phenoxy substituted with halo, ($C_1$–$C_3$) alkyl, ($C_1$–$C_3$)haloalkyl, nitro, ($C_1$–$C_3$)alkoxy, ($C_1$–$C_3$) haloalkoxy, or cyano;

$X_1$ is hydrogen, halo, or acetyl;

$X_2$ is hydrogen or halo;

$X_3$ is halo, cyano, or nitro;

$X_4$ is halo, ($C_1$–$C_8$)alkyl, ($C_1$–$C_4$)haloalkyl, ($C_1$–$C_4$) alkoxy, ($C_3$–$C_6$)cycloalkoxy, ($C_2$–$C_6$)alkenyloxy, ($C_3$–$C_6$)alkynyloxy, ($C_1$–$C_4$)alkoxycarbonyl, ($C_2$–$C_6$) alkenyloxycarbonyl, ($C_3$–$C_6$)alkynyloxycarbonyl, ($C_1$–$C_8$)alkylsulfonylamino, ($C_1$–$C_8$) alkylsulfonylalkylamino, ($C_1$–$C_4$) alkoxycarbonylmethoxy, or ($C_1$–$C_4$) alkoxycarbonylethoxy; and $X_5$ is hydrogen or halo;

and agronomically acceptable salts thereof.

3. The compound of claim 1 of the formula:

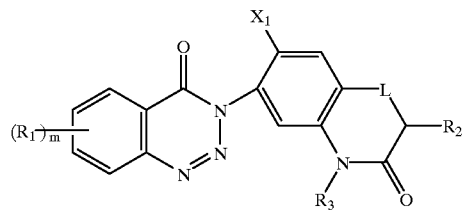

wherein m is from 1 to 4;

$R_1$ is hydrogen, halo, ($C_1$–$C_4$)alkyl, ($C_1$–$C_3$)haloalkyl, ($C_1$–$C_3$)alkoxy, ($C_1$–$C_3$)haloalkoxy, nitro, cyano, phenoxy, or phenoxy substituted with halo, ($C_1$–$C_3$) alkyl, ($C_1$–$C_3$)haloalkyl, nitro, ($C_1$–$C_3$)alkoxy, ($C_1$–$C_3$) haloalkoxy, or cyano;

L is O or S;

$X_1$ is H, Cl or F $R_2$ is H or ($C_1$–$C_3$)alkyl; and $R_3$ is ($C_1$–$C_6$)alkyl, ($C_1$–$C_6$)haloalkyl, ($C_3$–$C_6$)alkenyl, halo($C_3$–$C_6$)alkenyl, ($C_3$–$C_6$)alkynyl; halo($C_3$–$C_6$) alkynyl, alkoxyalkyl, alkenyloxyalkyl; alkynyloxy- alkyl; cyanoalkyl; amino, or hydroxy;

and agronomically acceptable salts thereof.

4. An herbicidal composition comprising one or more compounds of claim 1 and an agronomically acceptable carrier.

5. The herbicidal composition of claim 4, wherein the compound is of the formula:

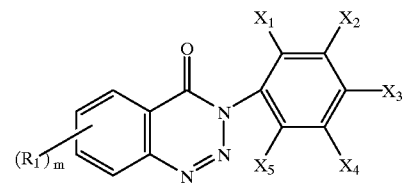

wherein:

m is from 1 to 4;

$R_1$ is hyrogen, halo, ($C_1$–$C_4$)alkyl, ($C_1$–$C_8$)haloalkyl, ($C_1$–$C_3$)alkoxy, ($C_1$–$C_3$)haloalkoxy, nitro, cyano, phenoxy, or phenoxy subitituted with halo, ($C_1$–$C_3$) alkyl, ($C_1$–$C_3$)haloalkyl, nitro, ($C_1$–$C_3$)alkoxy, ($C_1$–$C_3$) haloalkoxy, or cyano;

$X_1$ is hydrogen, halo, or acetyl;

$X_2$ is hydrogen or halo;

$X_3$ is halo, cyano, or nitro;

$X_4$ is halo, ($C_1$–$C_8$)alkyl, ($C_1$–$C_4$)haloalkyl, ($C_1$–$C_4$) alkoxy, ($C_3$–$C_6$)cycloalkoxy, ($C_2$–$C_6$)alkenyloxy, ($C_3$–$C_6$)alkynyloxy, ($C_1$–$C_4$)alkoxycarbonyl, ($C_2$–$C_6$) alkenyloxycarbonyl, ($C_3$–$C_6$)alkynyloxycarbonyl, ($C_1$–$C_8$)alkylsulfonylamino, ($C_1$–$C_8$) alkylsulfonylalkylamino, ($C_1$–$C_4$) alkoxycarbonylmethoxy, or ($C_1$–$C_4$) alkoxycarbonylethoxy; and $X_5$ is hydrogon or halo;

provided that when $X_1$ is halo and $X_2$ and $X_3$ are hydrogen or halo, then $X_4$ and $X_5$ are other than hydrogen, halo, ($C_1$–$C_8$)alkyl, or ($C_1$–$C_4$)haloalkyl;

and agronomically acceptable salts thereof.

6. The herbicidal composition of claim 4, wherein the compound is of the formula:

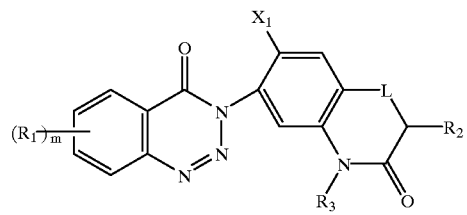

wherein m is from 1 to 4;

$R_1$ is hydrogen, halo, ($C_1$–$C_4$)alkyl, ($C_1$–$C_3$)haloalkyl, ($C_1$–$C_3$)alkoxy, ($C_1$–$C_3$)haloalkoxy, nitro, cyano, phenoxy, or phenoxy substituted with halo, ($C_1$–$C_3$) alkyl, ($C_1$–$C_3$)haloalkyl, nitro, ($C_1$–$C_3$)alkoxy, ($C_1$–$C_3$) haloalkoxy, or cyano;

L is O or S;

$X_1$ is H, Cl or F $R_2$ is H or ($C_1$–$C_3$)alkyl; and $R_3$ is ($C_1$–$C_6$)alkyl, ($C_1$–$C_6$)haloalkyl, ($C_3$–$C_6$)alkenyl, halo($C_3$–$C_6$)alkenyl, ($C_3$–$C_6$)alkynyl; halo($C_3$–$C_6$) alkynyl, alkoxyalkyl, alkenyloxyalkyl; alkynyloxy- alkyl; cyanoalkyl; amino, or hydroxy;

and agronomically acceptable salts thereof.

7. A method for controlling unwanted vegetation comprising applying to the unwanted vegetation, or to the soil wherein the unwanted vegetation grows, an herbicidally effective amount of one or more compounds of claim 1 or the composition of claim 4.

8. The method of claim 7, wherein the compound is of the formula:

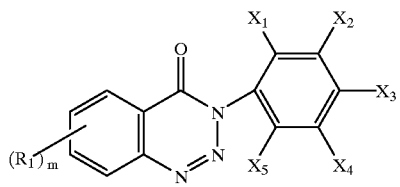

wherein:

m is from 1 to 4;

$R_1$ is hydrogen, halo, $(C_1-C_4)$alkyl, $(C_1-C_3)$haloalkyl, $(C_1-C_3)$alkoxy, $(C_1-C_3)$haloalkoxy, nitro, cyano, phenoxy, or phenoxy substituted with halo, $(C_1-C_3)$alkyl, $(C_1-C_3)$haloalkyl, nitro, $(C_1-C_3)$alkoxy, $(C_1-C_3)$haloalkoxy, or cyano;

$X_1$ is hydrogen, halo, or acetyl;

$X_2$ is hydrogen or halo;

$X_3$ is halo, cyano, or nitro;

$X_4$ is halo, $(C_1-C_8)$alkyl, $(C_1-C_4)$haloalkyl, $(C_1-C_4)$alkoxy, $(C_3-C_6)$cycloalkoxy, $(C_2-C_6)$alkenyloxy, $(C_3-C_6)$alkynyloxy, $(C_1-C_4)$alkoxycarbonyl, $(C_2-C_6)$alkenyloxycarbonyl, $(C_3-C_6)$alkynyloxycarbonyl, $(C_1-C_8)$alkylsulfonylamino, $(C_1-C_8)$alkylsulfonylalkylamino, $(C_1-C_4)$alkoxycarbonylmethoxy, or $(C_1-C_4)$alkoxycarbonylethoxy; and $X_5$ is hydrogen or halo;

and agronomically acceptable salts thereof.

9. The method of claim 7, wherein the compound is of the formula:

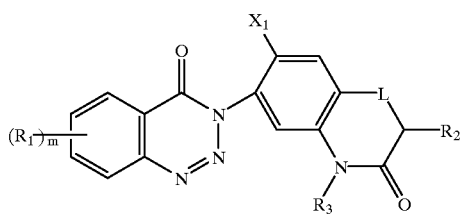

wherein m is from 1 to 4;

$R_1$ is hydrogen, halo, $(C_1-C_4)$alkyl, $(C_1-C_3)$haloalkyl, $(C_1-C_3)$alkoxy, $(C_1-C_3)$haloalkoxy, nitro, cyano, phenoxy, or phonoxy substituted with halo, $(C_1-C_3)$alkyl, $(C_1-C_3)$haloalkyl, nitro, $(C_1-C_3)$alkoxy, $(C_1-C_3)$haloalkoxy, or cyano;

L is O or S;

$X_1$ is H, Cl or F $R_2$ is H or $(C_1-C_3)$alkyl; and $R_3$ is $(C_1-C_6)$alkyl, $(C_1-C_6)$haloalkyl, $(C_3-C_6)$alkenyl, halo$(C_3-C_6)$alkenyl, $(C_3-C_6)$alkynyl; halo$(C_3-C_6)$alkynyl, alkoxyalkyl; alkenyloxyalkyl; alkynyloxyalkyl; cyanoalkyl; amino, or hydroxy;

and agronomically aeceptable salts thereof.

* * * * *